(12) United States Patent
Li et al.

(10) Patent No.: US 12,399,921 B2
(45) Date of Patent: Aug. 26, 2025

(54) EXTRACTION OF PATIENT-LEVEL CLINICAL EVENTS FROM UNSTRUCTURED CLINICAL DOCUMENTATION

(71) Applicant: PENTAVERE RESEARCH GROUP INC., Toronto (CA)

(72) Inventors: Wenkai (Aaron) Li, Toronto (CA); Steven Aviv, Toronto (CA)

(73) Assignee: PENTAVERE RESEARCH GROUP INC.

(*) Notice: Subject to any disclaimer, the term of this patent is extended or adjusted under 35 U.S.C. 154(b) by 0 days.

(21) Appl. No.: 18/195,168

(22) Filed: May 9, 2023

(65) Prior Publication Data

US 2023/0367799 A1  Nov. 16, 2023

Related U.S. Application Data

(60) Provisional application No. 63/340,247, filed on May 10, 2022.

(51) Int. Cl.
*G06F 16/334* (2025.01)
*G06N 20/00* (2019.01)

(52) U.S. Cl.
CPC ......... *G06F 16/3347* (2019.01); *G06N 20/00* (2019.01)

(58) Field of Classification Search
CPC .... G06F 16/3347; G06N 20/00; G06N 5/045; G06N 3/0455; G06N 3/088; G06N 3/0895; G06N 3/09; G16H 10/20; G16H 10/60; G16H 15/00

See application file for complete search history.

(56) References Cited

U.S. PATENT DOCUMENTS

| 12,210,839 | B1* | 1/2025 | Burton | G06F 16/3344 |
| 2011/0153362 | A1* | 6/2011 | Valin | G06Q 20/1085 |
| | | | | 340/5.82 |
| 2011/0236864 | A1* | 9/2011 | Ashford | G16H 20/70 |
| | | | | 434/236 |
| 2016/0160263 | A1* | 6/2016 | Whitney | C12Q 1/37 |
| | | | | 435/23 |

(Continued)

*Primary Examiner* — Angelica Ruiz

(57) ABSTRACT

Some embodiments of the present disclosure provide a framework for using unsupervised artificial intelligence to automatically abstract and align clinical facets. The approach of the present application may be shown to reduce human involvement and, accordingly, enhance privacy compliance. Aspects of the present application relate to a process of self-learning from the data available. Accordingly, aspects of the present application may be shown to be resilient to the appearance of new concepts and facets in future data. Additionally, aspects of the present application may be shown to adapt well when presented with different languages, different styles of documentation and different clinical domains. Aspects of the present application relate to processing unstructured, non-fielded data, such as clinical notes, admission and discharge summaries, surgical notes, lab reports and imaging reports. These notes may be considered to contain hidden insights in the clinical domain. Additionally, these notes may be considered to contain data that may not be captured elsewhere in a readily usable way. Aspects of the present application may be shown to support analysis of large size populations at a relatively low incremental cost.

15 Claims, 4 Drawing Sheets

(56) References Cited

U.S. PATENT DOCUMENTS

| | | | |
|---|---|---|---|
| 2019/0272907 A1* | 9/2019 | Aldairy | G16H 15/00 |
| 2020/0248273 A1* | 8/2020 | Johnson | C12Q 1/6886 |
| 2022/0138572 A1* | 5/2022 | Song | G06N 3/045 |
| | | | 706/20 |
| 2022/0147770 A1* | 5/2022 | Jain | G06F 18/217 |
| 2022/0180447 A1* | 6/2022 | Kearney | G06N 3/047 |
| 2022/0318621 A1* | 10/2022 | Gong | G06N 3/006 |
| 2023/0022845 A1* | 1/2023 | Meng | G06F 40/279 |
| 2023/0104662 A1* | 4/2023 | Fatemi | G06N 3/045 |
| | | | 704/9 |

* cited by examiner

EXTRACTION OF PATIENT-LEVEL CLINICAL EVENTS FROM UNSTRUCTURED CLINICAL DOCUMENTATION

CROSS-REFERENCE TO RELATED APPLICATIONS

The present application claims priority to U.S. Provisional Application Ser. No. 63/340,247, filed May 10, 2022, the contents of which are hereby incorporated herein by reference.

TECHNICAL FIELD

The present disclosure relates, generally, to processing unstructured clinical documentation and, in particular embodiments, to extraction of patient-level clinical events from unstructured clinical documentation.

BACKGROUND

The state of the art for dealing with processing unstructured clinical documentation may be shown to be a manual abstraction approach. That is, unstructured clinical documentation may be processed using people to populate a timeline with data. It may be considered that the manual abstraction approach is error-prone and expensive.

Typically, study populations are too small and the clinical facets considered too narrow for broader application.

There exist various artificial intelligence (AI) approaches to processing unstructured clinical documentation. These approaches may use AI classifiers and AI entity recognizers, found in the public domain, to solve specific, well-defined problems on unstructured clinical documentation. These approaches may be used to, for one example, find all drug mentions or to, for another example, classify a particular patient as a smoker or a non-smoker.

There are approaches that are based on structured or fielded data, which are little more than dashboards presenting any readily available data in a nice way.

These inventions rely on data being collected in a structured way to start, which is typically not the case with clinical data.

SUMMARY

Aspects of the present application relate to use of unsupervised AI to automatically abstract and align clinical facets. The approach of the present application may be shown to reduce human involvement and, accordingly, enhance privacy compliance. Aspects of the present application relate to a process of self-learning from the data available. Accordingly, aspects of the present application may be shown to be resilient to the appearance of new concepts and facets in future data. Additionally, aspects of the present application may be shown to adapt well when presented with different languages, different styles of documentation and different clinical domains. Aspects of the present application relate to processing unstructured, non-fielded data, such as clinical notes, admission and discharge summaries, surgical notes, lab reports and imaging reports. These notes may be considered to contain hidden insights in the clinical domain. Additionally, these notes may be considered to contain data that may not be captured elsewhere in a readily usable way. Aspects of the present application may be shown to support analysis of large size populations at a relatively low incremental cost.

Known approaches to processing unstructured clinical documentation are not known to present an entire view of a patient and are not known to be resilient to the emergence of new concepts. That is, existing approaches typically require substantial effort to gather new data to retrain. Accordingly, existing approaches are not known to adapt well to different styles of documentation. It is notable that an oncology style of documentation may be distinct from a family medicine style of documentation.

Manual abstraction is extremely time consuming and error-prone, does not scale to large populations, and is contrary to privacy by design as people see the private data of patients.

Approaches based upon traditional supervised AI models may be shown to involve a large manual effort to label data for training, which suffers the same limitations as manual abstraction. Further, once the model is trained on a first set of training data, there is no guarantee that the trained model will work well on a second set of data. This may be especially true if the style of the second set of data is different from the style of the first set of training data. Accordingly, the trained model may not be useful in specific clinical domains.

According to aspects of the present application, there is provided a method. The method includes accessing unstructured clinical documentation, converting the unstructured clinical documentation to vector representations, using an artificial intelligence (AI) model to encode the vector representations to obtain embeddings and processing the embeddings.

BRIEF DESCRIPTION OF THE DRAWINGS

For a more complete understanding of the present embodiments, and the advantages thereof, reference is now made, by way of example, to the following descriptions taken in conjunction with the accompanying drawings, in which.

DETAILED DESCRIPTION OF ILLUSTRATIVE EMBODIMENTS

For illustrative purposes, specific example embodiments will now be explained in greater detail in conjunction with the figures.

The embodiments set forth herein represent information sufficient to practice the claimed subject matter and illustrate ways of practicing such subject matter. Upon reading the following description in light of the accompanying figures, those of skill in the art will understand the concepts of the claimed subject matter and will recognize applications of these concepts not particularly addressed herein. It should be understood that these concepts and applications fall within the scope of the disclosure and the accompanying claims.

Moreover, it will be appreciated that any module, component, or device disclosed herein that executes instructions may include, or otherwise have access to, a non-transitory computer/processor readable storage medium or media for storage of information, such as computer/processor readable instructions, data structures, program modules and/or other data. A non-exhaustive list of examples of non-transitory computer/processor readable storage media includes magnetic cassettes, magnetic tape, magnetic disk storage or other magnetic storage devices, optical disks such as compact disc read-only memory (CD-ROM), digital video discs or digital versatile discs (i.e., DVDs), Blu-ray Disc™, or other optical storage, volatile and non-volatile, removable and non-removable media implemented in any method or technology, random-access memory (RAM), read-only memory (ROM), electrically erasable programmable read-only memory (EEPROM), flash memory or other memory technology. Any such non-transitory computer/processor storage media may be part of a device or accessible or connectable thereto. Computer/processor readable/executable instructions to implement an application or module described herein may be stored or otherwise held by such non-transitory computer/processor readable storage media.

Aspects of the present application relate to preparation of "subject journals" from notes, without any human involvement.

A "subject" is the particular person to whom a particular subject journal relates. That is, a "subject" may be a patient or a clinical trial participant. Accordingly, alternate terms for "subject journal" include "patient journal" and "clinical trial participant journal."

A "journal" may be understood to contain "entries" arranged by "facet" through time.

A "facet" is an attribute of the subject, such as a medication or a comorbidity. Aspects of the present application relate to automatically discovering facets.

An "entry" is a sentence from the notes that is determined to be both relevant and related to the facet. A facet is expected to contain multiple entries.

Figure 1:
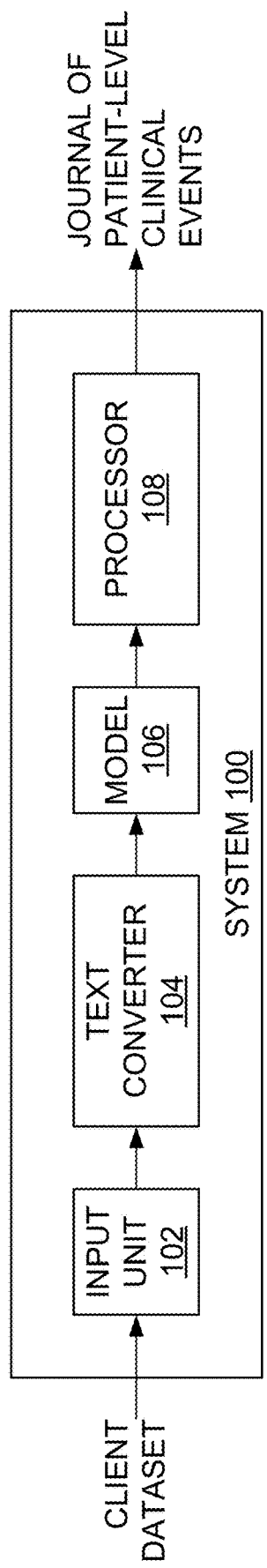
FIG. 1 illustrates, as a block diagram, a system for carrying out aspects of the present application, the system including a model and a processor.

FIG. 1 illustrates, as a block diagram, a system 100 for carrying out aspects of the present application. The system 100 includes an input unit 102 connected so as to allow the system 100 to access a client dataset. A model 106 connects to the input unit 102 through a text converter 104. A processor 108 is connected to the model 106 to receive output from the model 106 and provide output for the system 100.

Figure 2:
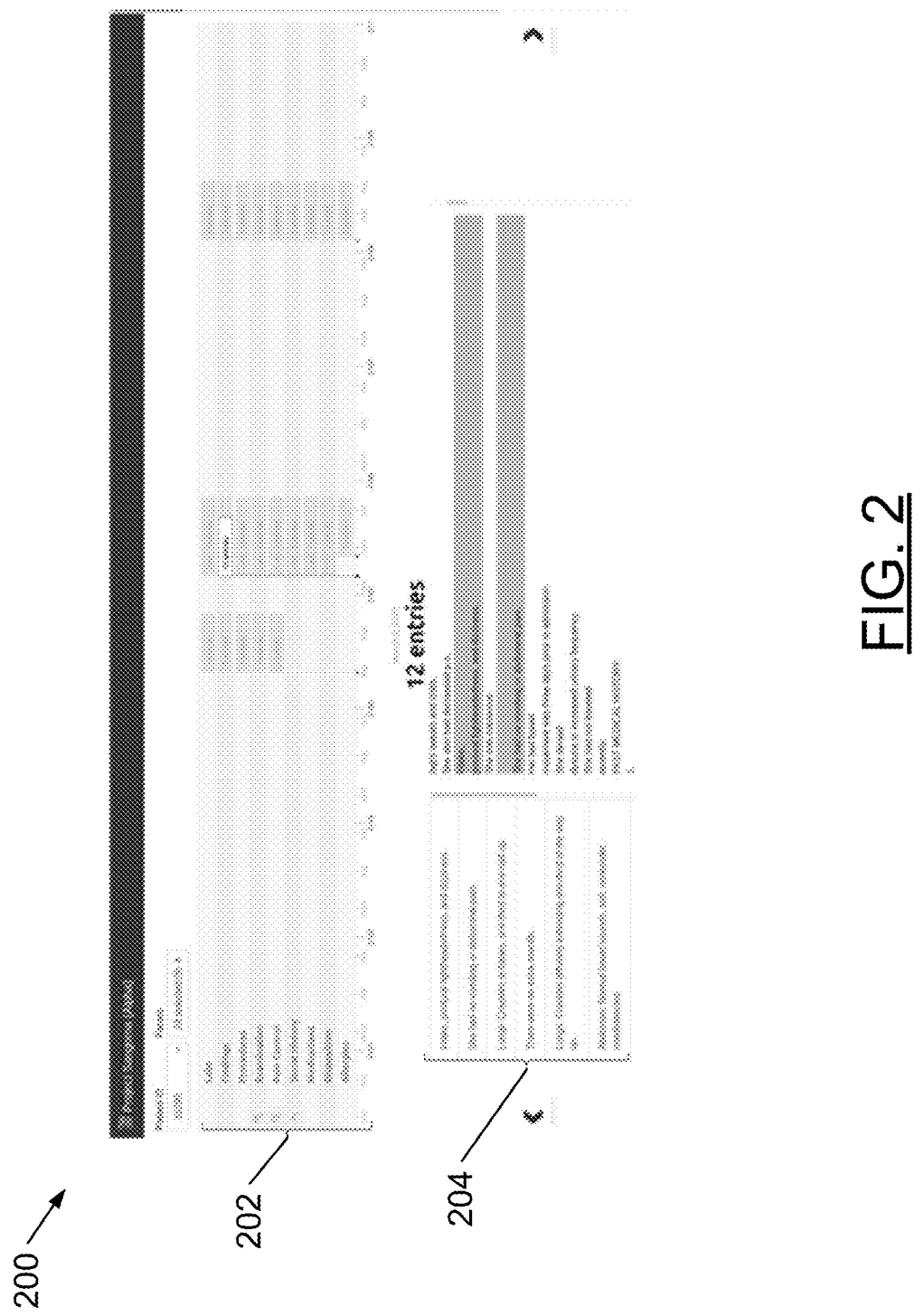
FIG. 2 illustrates a screenshot presenting output from the processor of FIG. 1 in a user-friendly way, in accordance with aspects of the present application.

FIG. 2 illustrates a screenshot 200 presenting output from the processor 108 of FIG. 1 in a user-friendly way. A top portion 202 of the screenshot 200 includes a journal summary. The journal summary includes indications of clinical facets discovered by the model 106 and a summary of a number of entries per facet through time.

Subject journals may be shown to be commercially advantageous at the most basic, patient-facing level. Indeed, subject journals may be shown to allow clinicians to rapidly understand a patient's experience through time. It is known for clinicians to rely on the patient to remember details of patient's experience through time. Alternatively, the clinician may be expected to spend substantial time reviewing previous notes.

A lower portion 204 of the screenshot 200 may be considered to allow the user to examine details of each event. The lower portion 204 of the screenshot 200 may also be considered to allow the user to drill-down all the way to the source text to see the events in context.

Aspects of the present application relate to deploying a deep learning model (see the model 106 of FIG. 1) on a client machine for processing unstructured client data. In one aspect, the approach may be implemented entirely without human intervention. In another aspect, the approach may be implemented in a guided manner wherein the approach efficiently collaborates with human experts. Aspects of the present application that are designed to operate without human intervention relate to a system that can highlight, summarize and generate patient journeys. Aspects of the present application that are designed to operate with human experts relate to a system that can highlight vital information, drastically reduce time spent on reading medical documents, facilitate manual reviews or capture potential mistakes with human experts in the loop.

It may be considered that there has been an explosion of health data over the last few years, in both the volume of health data and the velocity of health data.

Despite the promise of the known electronic health record (EHR) to organize data, a large amount of data is still collected as free-form narrative. Furthermore, it may be shown that there exists an immense backlog of free-form narrative data. Patient journeys are advantageous at the level of direct patient care, as patient journeys may be shown to allow clinicians to rapidly understand the patient experience through time. Previously, it was known for the clinicians to rely on the patient to remember details of a patient experience. Alternatively, it was known for the clinician to spend substantial time reviewing previous notes and documents within an EHR. Well-constructed and conceptually aligned patient journeys may be shown enable the comparison and contrasting of a given patient to another patient or groups of patients to groups of patients. Such patient journeys may be shown to support multiple real-world use cases. Example real-world use cases include research use cases and drug development use cases. Further example real-world use cases include clinical trial recruitment use cases, including those use cases related to diversity, equity and inclusion initiatives. Additional example real-world use cases include clinical trial forensic use cases, wherein one goal is to maximize a probability of a successful trial. Still further example real-world use cases include clinical quality improvement use cases, population health initiative use cases and use cases related to patient identification in rare diseases. Even further example real-world use cases include clinical practice assessment use cases that are used to assess adherence to standards of care.

Some aspects of the present application relate to a patient cohort task. Further aspects of the present application relate to an individual patient journey task. These tasks may be shown to emphasize modelling a semantic "medical facet" or, in a broader sense, modelling a "semantic facet." When aspects of the present application are applied to other industries, like financial text data, it may be more appropriate the "semantic facet" term.

Each facet may be shown to have a plurality of properties.

One facet property is called "fluent importance." The importance of a given facet may be unknown until runtime deployment, when data is acquired. For example, one of the facets with relatively high importance in cancer research is "metastases." However, for a case in which a dataset and a corresponding patient population relate to a given study that is focused on heart attacks, the facet metastases may be considered to have relatively low importance. Further, important facets may be under-represented in the context of all the text in the sense that, while the metastases facets are important, the metastases facets may be mentioned only infrequently relative to all the other text.

Another facet property is called an "unknown similarity and distance matrix." The unknown similarity and distance matrix property of a given facet relates to a degree to which the given facet may vary depending on a targeted objective.

A "shallow" version of the unknown similarity and distance matrix property may be defined, within academic settings, as "semantic text similarity," i.e., the value of the property may indicate a degree to which two sentences are semantically the same.

A "deep" version of the unknown similarity and distance matrix property may be defined for "medical facets" that act as clues. Rather than introducing individual scientific facts and previously known observations, the value of the property may indicate an extent to which a given facet is difficult to determine, even with trained eyes. Indeed, the given facet may have not been adequately defined and studied.

The difficulty of determining the facet may be resolved, in computer science, at inference time with standard techniques. For one example, an unknown similarity and distance matrix property for a given facet may be determined using cosine distance as a runtime parameter.

However, two questions remain.

The first question relates to how to train and preserve both higher-level similarities and lower-level similarities at scale at training time. Such training and preserving at scale may be considered difficult due to a distance function that has been derived either too high or low during the training phase. On one hand, models that are currently deployed in the medical field may be considered to be too general to provide utility. On the other hand, models that are currently deployed in the medical field may be considered to only produce results that are so detailed that the results cannot be transferred in aid of generating high-level insights.

The second question relates to whether the cosine distances benefit from runtime adjustment. In a case wherein the cosine distances benefit from runtime adjustment, then manual engineering efforts may be involved, with additional medical support. Even though the manual engineering efforts may be minimal, it may be shown that it is hard to use a single value to fit all samples, because the texts within the runtime dataset usually do not have uniform space (pseudo-metric) that can be used to fit the semantic meaning of the texts. For one example, in the cases of head and neck cancer, information about lung metastasis may be separated from information about brain metastasis, because the progression of diseases is more severe at the lung. In contrast, when studying lung cancer, the separation of the information about lung metastasis from information about brain metastasis is not carried out, because both cases count as metastasis status.

Another facet property is called "coupled knowledge." It is known that sematic texts often provide coupled context in a medical dataset. Consider the example text, "The right coronary arteries showed diffuse disease but had no flow-limiting lesions." The example text provides at least two medical facets. More important than providing at least two medical facets, the text indicates an uncommon patient condition that should be noticed compared with the typical relationship between coronary arteries disease and lesions. Accordingly, it is preferable that the example text is noticed, by a physician, as containing crucial information.

The coupled knowledge property of a facet may be expected to appear often in the medical dataset.

Industry models in current deployment may be shown to perform a too-detailed analysis that captures two facets but ignores the context. That is, industry models in current deployment may place too much focus on one facet. This placement of too much focus on one facet may be considered to be due to common disadvantages of deep learning pipelines and model designs.

Notably, it may be illustrated that these properties may not be resolved and modelled directly with current state-of-the-art models and pipeline design.

Aspects of the present application relate to reducing the above problems proposed when modelling medical facets. Modelling medical facets may be shown to enable many vital applications and increase efficacy in healthcare system in which the modelling is deployed.

With particular application with respect to common conditions related to medical documents in North America and Europe, aspects of the present application relate to designs and deployments that may be shown to be valuable for working within government data regulations, within strict patient privacy conditions and consent models and within contractual agreements.

With recent advancements and experiments, it may be shown that deep learning models, like transformer-based models, perform Natural Language Processing (NLP) tasks exceedingly well. However, one of the main problems associated with applying recent state-of-the-art models to a medical domain is that the model may be unable to adapt or transfer knowledge well under relative unknown semantics and context. The disadvantage may be shown to limit the abilities for modelling treatment and progression, possible strange errors, patient journey and many other everyday medical tasks and operations required to conduct.

Aspects of the present application relate to allowing a model to perform and inference stably under real industry deployments of deep learning models that were previously unfavorable for deep learning. In particular, it may be shown that procedure and deployment aspects of the present application allow models to generalize knowledge and information. Through such generalization, the model may be able to effectively apply and transfer the knowledge under the same subdomain with ease.

In addition, aspects of the present application have been tested and validated on sectors outside of the medical sector, such as the financial sector.

Aspects of the present application relate to a training stage during which stage the model 106 (FIG. 1) may be trained. Upon completion of the training, the model 106 is operable to receive, as input, vector representations of input text and produce, as output, embedding vectors. The embedding vectors may be understood to represent the input text.

Other aspects of the present application relate to an inference stage, which stage may also be called a deployment stage. In the inference stage, output from the model 106 may be used by the processor 108, in combination with additional patient and document meta information, to produce a medical journey for a particular patient. In the inference stage, patients may be compared via cohorts, with or without so-called conditions of interest.

Figure 3:
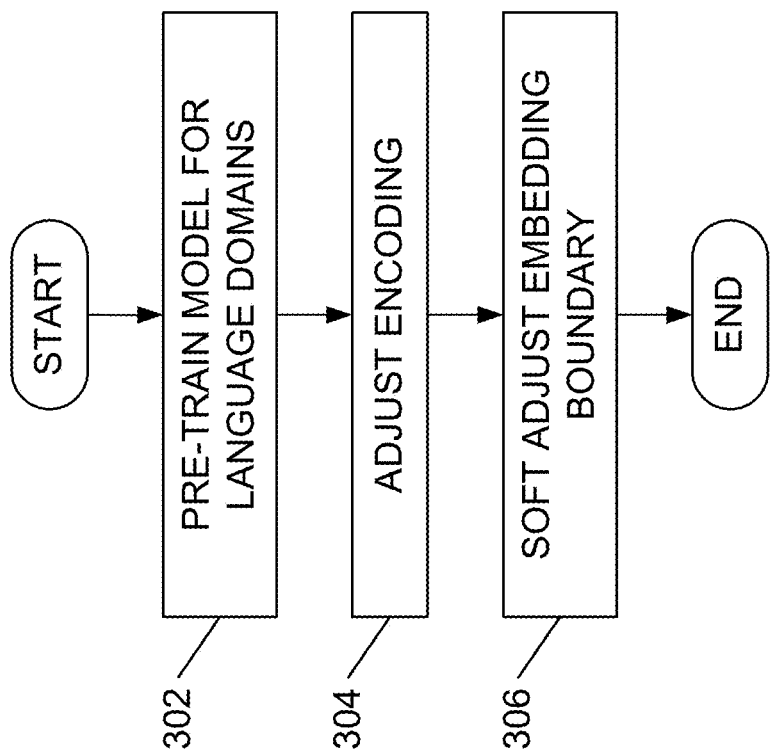
FIG. 3 illustrates example steps in a training stage, wherein the model of FIG. 1 is trained to, in a later inference stage, allow the system of FIG. 1 to produce a medical representation of input text, in accordance with aspects of the present application.

FIG. 3 illustrates example steps in the training stage, wherein the model 106 is trained to, in a later inference stage, allow the system 100 to produce medical representation of input text.

One objective of the training stage is to obtain a model that can encode text to a vector that is an as-accurate-as-practical representation of semantics for the text in the context of a given subdomain. In the present application, the English medical subdomain is presented as an example subdomain.

Initially, the model may be pre-trained (step 302) for language domains. In one example, the language domain for which the model may be pre-trained (step 302) is English. It should be clear that alternatively, or additionally, the model may be trained for other languages. The pre-training (step 302) of the model may also involve pre-training in a language sub-domain. Of interest in the present application is the English medical sub-domain. However, it should be clear that the pre-training (step 302) of the model may also involve pre-training in other language sub-domains, such as an English financial sub-domain. Conveniently, pre-training in a particular sub-domain may be shown to boost performance in the particular sub-domain.

For illustration purposes, the known BERT model is used in the following for the model 106 of FIG. 1.

The BERT model is an open source machine learning framework for natural language processing (NLP). The BERT model is designed to help computers understand the meaning of ambiguous language in text by using surrounding text to establish context. The BERT model was pre-trained using text from Wikipedia and can be fine-tuned with question and answer (QA) datasets. It should be clear that other transformer-based models may be used in place of the BERT model.

The pre-training (step 302) of the model may make use of massive English texts, thereby allowing the model to acquire general language understandings.

The initial text data used in the pre-training (step 302) of the model may be consistent with text dumps from the Internet, e.g., Wikipedia, Book corpus.

Later, further training, with a lower learning rate, may be carried out. The further training portion of the pre-training (step 302) of the model may be use medical text data, e.g., emergency room discharge data and cancer research text data. The further training portion of the pre-training (step 302) of the model may be shown to allow the model to learn a medical context in more detail than is available to be learned from the initial text data.

The pre-training (step 302) may be directed to preparing the model to carry out two tasks. One of the tasks is a mask infill task. The mask infill task may make use of a Mask Language Model, "MLM." The other one of the tasks is a next sentence prediction (NSP) task. Both tasks may be understood to follow a more traditional approach of transformer pretraining.

The MLM may be shown to allow the model to learn token context. The text converter 104 may randomly select a token within a given sentence. The text converter 104 may then apply masking to mask the token in the given sentence before using the model 106 to encode the given masked sentence. The processor 108 may then predict a degree to which the given sentence is similar in context to another sentence, based on a distance between embedding vectors formed on the basis of the two sentences.

For general English training, 15% of the tokens may be masked.

For more specific medical context training, 30% of the tokens may be masked.

The BERT model includes an encoder. The BERT model also includes a classification layer. The classification layer is positioned to receive output from the encoder. The classification layer may then employ a softmax function to classify the output of the encoder.

The known softmax function takes, as input, a vector, z, of K components. The components are real numbers. The known softmax function normalizes the vector into a probability distribution. The probability distribution includes K probabilities, with each probability proportional to the input numbers. That is, prior to applying softmax, some of the vector components could be negative, or greater than one. Furthermore, the vector components might not sum to 1. After applying softmax, each component will be in the interval (0,1) and the components will add up to 1, so that the components can be interpreted as probabilities.

A text passage (i.e., a sentence) that contains N words may be converted, by the text converter 104, so that the text passage is represented by N variables:

$$w_1, w_2, w_3, \ldots, w_{t-1}, w_t, w_{t+1}, \ldots, w_{N-1}, w_N.$$

The BERT-based encoder acts to predict, for a given word, $w_t$, word position. That is, the BERT-based encoder acts to predict, for a given word, $w_t$, the value of t in the interval 1 to N, inclusive.

The encoder acts to learn, for a given word, word context and word position. The encoder may then infer a predictive power of the given word over the context of the sentence from which the word has been taken. As is known, the ability to infer the predictive power of the word may be obtained by training the encoder to predict a masked position token.

In aspects of the present application, the medical tokens are masked with higher probabilities to customize the training for medical contexts. The higher probabilities may be scaled with a constant value. Each token has a probability of being a medical token, with the probability typically applied as overlap to a standard medical dictionary.

It is known to apply attention mechanisms, such as self-attention and encoder-decoder attention, for learning in model architecture design. The attention mechanisms use the following equations to optimize a score using scaled dot product attention in each of a plurality of transformer blocks.

$$\mathrm{softmax}\left(\frac{QK^T}{\sqrt{d_k}}\right)V$$

where Q is a query, K is a key and V is a value in standard transformer training. Additionally, $d_k$ refers to a size of the query. The variables Q and K before the linear layers and after dot product as above, may be normalized by the size of the query, $d_k$. The blocks are often applied within the model architecture and merge attention scores by softmax for the final attention score. The softmax function compresses the input attention vectors to a value between 0 and 1.

The softmax function may be defined in a standard form for an input, $x_i$, and a plurality of candidate outputs, $x_j$, as follows:

$$\mathrm{softmax}(x_i) = \frac{e^{x_i}}{\Sigma_j e^{x_j}}.$$

The input to the BERT-based encoder is to be a single sequence.

It is known for input to BERT-based encoders use a special token [CLS] and a special token [SEP] to allow the BERT-based encoder to properly handle the input. The [SEP] token is inserted at the end of a single input. When a task involves more than one input, the [SEP] token helps the BERT-based encoder to recognize the end of one input and the start of another input within a single input. Tasks that are known to involve more than one input include natural language inference (NLI) tasks and QA tasks.

Inserting the special [CLS] token and the special [SEP] token when encoding input for presentation to the BERT-based encoder may lead to the following example input:

[CLS] TEXT *A* [SEP] TEXT *B* [SEP].

In the example input, TEXT A indicates an input sentence and TEXT B indicates an output sentence. The task that the BERT-based encoder is intended to carry out involves determining a prediction regarding whether TEXT B is likely to follow TEXT A. The BERT-based encoder may express the prediction as a binary state. A set of "imposters" (also known as negative samples) may be added into a batch of training samples. In imposter input may appear as:

[CLS] TEXT *C* [SEP] TEXT *D* [SEP].

The words in the "TEXT C" and "TEXT D" may, for example, be sampled randomly from the dataset of words in the set of words used when training the BERT-based encoder. It is generally assumed that a second set of randomly sampled text (e.g., TEXT D) will not, in general, follow a first set of randomly sampled text (e.g., TEXT C) in semantic context.

Aspects of the present application have an objective to cause the BERT-based encoder to learn a vector representation of any input text. It may then be stated that the BERT-based encoder implements a hypothesis function, E.

In those situations wherein the model 106 is implemented as a transformer-based model, each embedding may be acquired by pooling the hidden state from the model, commonly referred to as CLS pooling. The procedure involves pooling the hidden state of the first token position, which is occupied by a unique [CLS] token.

The embedding process can be defined, informally, as a program that implements:

$$E(\text{TEXT } A) = \text{Transformer}(\text{TEXT } A) \cdot \text{last}_{hidden}$$

Subsequent to the pre-training (step 302), the model 106 may be adjusted (step 304). In particular, the encoding carried out by the model may be adjusted (step 304) via a QA training schema. The QA training schema may involve the use of a "passive anchor." The QA training schema may be shown to train the model to improve the logical semantic inference abilities of the model. The training adjustment (step 304) may employ a general QA asymmetrical encoding ranking with the "passive anchor."

The adjusting (step 304) of the model aims to minimize a loss. The QA training schema involves providing a question as input to the model. The question provided is associated with an expected answer. A difference between the output from the model and the expected answer may be expressed as the loss that is to be minimized. It may be considered that, among all possible outputs from the model, the expected answer may occupy a position. Outputs from the model that are close, in position, to the expected answer may be said to be "inside the sematic neighborhood" of the expected answer.

The loss may be determined using a log-likelihood function.

The log-likelihood function may be arranged to provide a negative result for an output from the model that is outside sematic neighborhood of the expected answer. This technique may be defined as having a "passive anchor" for the model.

One reason for adjusting (step 304) the model through the use of a QA schema model is to stabilize the model encoding. At the inference time, there is an expectation that the model will work with unknown texts and under unknown contexts. Traditionally, this expectation is unfavorable for machine learning models or for deep learning models, because overfitting problems and other problems frequently surface. In response to a given model being trained for advanced and specified tasks with a targeted dataset, it may be shown that the given model will tend toward providing output in the targeted dataset, thereby resulting in overfitting results. Models may be trained on observations obtained from industry applications. However, it may be found that models trained in this way have suboptimal output. Output may be called suboptimal when a model fails to adapt to detailed domains. It follows that, without additional fine-tuning, machine learning models trained on observations obtained from industry applications can, when applied to specific medical scenarios, only derive insights that are too general or are incorrect. It has been noted that most, if not all, current machine learning models for specific medical scenarios are trained on observations obtained from industry applications and do not employ additional fine-tuning. These current machine learning models appear to attempt to get around the problems associated with not employing additional fine-tuning through the use of human effort and financial support. The adjusting (step 304) the model through the use of a QA schema with a passive anchor, which adjusting is characteristic of aspects of the present application, may be shown to urge the model to stabilize the encoding by isolating the logic context of the text input. Conveniently, the passive anchor aspects of the present application may be shown to run without logical context at runtime to "simulate" the context within. The passive anchor aspects of the present application may be shown to exhibit the primary advantages of state-of-the-art models as transformers while, in real-world settings, working around known design disadvantages of state-of-the-art models.

Another reason for adjusting (step 304) the model through the use of a QA schema model is to decouple knowledge.

The adjusting (step 304) the model through the use of a QA schema with a passive anchor, which adjusting is characteristic of aspects of the present application, may be shown to produce encodings that are more decoupled, than the encoding produced using known models, from specific aspects of medical treatments, medical terms, patient conditions or other related medical concepts.

In practice, such improved knowledge decoupling may be shown to provide a plurality of previously hard-to-acquire benefits for deep learning models. One example hard-to-acquire benefit is a feature called "high explainability." High explainability is desired for AI models that are used in medical fields. Unfortunately, high explainability often lacking in known solutions. Conveniently, the improved knowledge decoupling brought about through the adjusting (step 304) of the model through the use of a QA schema with a passive anchor.

Aspects of the present application relate to a model on top of which other applications may be allowed to reside. Conveniently, an application residing on top of a model representative of aspect of the present application may be shown to produce journeys and cohorts that may only be known at inference time. That is, the journeys and cohorts depend on the client dataset.

The adjusting (step 304) of the model through the use of a QA schema with a passive anchor involves training a model to select one answer passage from among a plurality of possible answer text passages. The model may carry out the selecting based on an input that may be called a question text passage, Q. The plurality of possible answer text passages includes a single correct answer text passage, $a_{correct}$, and a plurality of incorrect answer text passages, $a_{incorrect}$. Each time the model selects an answer text passage based on a question text passage, the answer text passage may be associated with a score. The score associated with the correct answer text passage, $a_{correct}$, is greater than the score that is associated with the incorrect answer text passages, $a_{incorrect}$.

The question text passage may be represented by a question vector, E(Q). Each of the answer text passages in the plurality of possible answer text passages may be represented by a corresponding answer vector, E(a). In such a case, the score may be determined, at runtime, as a dot product of the question vector and the answer vector:

$$score(Q,a) = (E(Q))^T \cdot E(a).$$

A plurality of scores may be obtained using the score function, score(Q,a), in view of a plurality of question text passages, Q, and a corresponding plurality of answer text passages, a, that have been obtained by providing the question text passages, Q, to the model. Notably, each score of the plurality of scores may be ranked at runtime.

A probability, $P(a_{given}=a_{correct}|Q)$, of a given answer text passage, $a_{given}$, being a correct answer text passage, $a_{correct}$, among an amount, n, of passages given the question text passage, Q, can be represented as a quotient of estimated joint probabilities:

$$P(a_{given} = a_{correct} | Q) = \frac{P(Q, a_{correct})}{\sum_{1}^{n} P(Q, a_{incorrect})}.$$

Where the joint probabilities may be estimated using a standard exponential function for non-linear estimation, E:

$$p(Q,a) \propto e^{E(Q,a)}.$$

In aspects of the present application, a training configuration includes a training batch that has n choices of passages in total and one positive passage. By assigning the correct answer with a probability of 1.0, the training loss of a score function, given a question and correct answer pair $(Q, a_{correct})$, may be applied to represent as:

$$Loss(Q, a_{correct}) = -score(Q, a_{correct}) + \log \sum_{1}^{n} e^{score(Q, a_i)}$$

Obtaining a score to associate with a question text passage, Q, and an answer text passage, a, may involve implementing the following loss function:

$$score(Q,a) = Loss[(E(Q))^T \cdot E(a)].$$

In step 304, the model 106 is initially trained on a large-scale training dataset. The initially training may be shown to teach basic logic and QA abilities in English.

The large-scale training dataset typically includes question-and-answer pairs manually curated from a Wikipedia data source.

This question-and-answer approach may be shown to allow the large-scale training dataset to have robust coverage of general human knowledge and logic.

After the initial training, the model may be trained on a limited set of question-answer pairs. The limited set may be sourced from medical datasets that range, for example, across cancer research data, genomic research data and emergency room data. The limited set may introduce various types of document, including research papers.

The model may be understood to have so-called "boundaries" that act to define subdomain-specific "neighborhoods."

Subsequent to adjusting (step 304) the encoding carried out by the model, the "soft" boundaries of the model may be adjusted (step 306). Conveniently, the soft boundary adjustment (step 306) may be shown to train the model to enhance the accuracy of the embeddings at the output of the model. For example, the accuracy of medical embeddings may be enhanced through the soft boundary adjustment (step 306).

In step 306, the soft boundary adjustment may be considered to be an attempt to correct the training dataset so that the training dataset has robust coverage of the medical dataset. The goal of step 306 is to improve the hypothesis function, E, so that the model 106 may generate an embedding responsive to receiving, as input, any text.

Conveniently, the hypothesis function, E, may be independently applied. That is, the hypothesis function, E, may be applied in the absence of a question text passage. It may be shown that the question text passage, discussed hereinbefore, acts as a passive anchor used in the training stage. The presence of a passive anchor, in training, may be shown to stabilize the subspace of embeddings. It follows that further corrections on the hypothesis function, E, may be performed in step 306.

As discussed hereinbefore, "medical facets" may not be observable and fluent until runtime. However, with the passive-anchor-based training regime described in the preceding, it may be recognized that there are two significant advantages that act as work-arounds for the lack of medical facet observability and fluency.

Step 306 may be shown to provide a model 106 that can encode all texts within an approximate semantic neighborhood. It follows that neighbor answers to a correct answer may be extracted.

It is known that the act of fine-tuning a model may require effort by human markers to implement a fragile process that, unfortunately, can cause overfit. The overfit may be blamed on the human markers inherently having biases. Furthermore, the human markers may only be able see dataset and knowledge introduced partially. Given a set of data with relatively balanced target domain coverage, texts within a vast scale of data may be acquired. The distance between the texts may be ranked. The information corrected at the dataset scale may be closely monitored.

Scaled training (FIG. 3) aspects of the present application may be considered to be beneficial for two reasons.

Conveniently, the scaled training aspects of the present application begin with a large amount of information and it is known that deep learning models may benefit significantly from a large amount of information.

Machine learning models are known to associate related but irrelevant concepts. Furthermore, machine learning models are known to learn incorrect ground truths due to direct or indirect correlations.

Accordingly, it may be considered convenient that the scaled training aspects of the present application may be shown to enable humans to quickly retrieve wrong information derived from such correlations. The humans may quickly correct the wrong information.

It may be shown that the scaled training aspects of the present application allow for determination of a most likely upper bound and a most likely lower bound of a distance between an incorrect answer text passage and a correct answer text passage. The lower bound may be determined on the basis of a concept overlap and a keyword overlap of the correct answer text passage with different semantic meanings. The higher bound may be determined on the basis of the incorrect answer text passage and the correct answer text passage having different expressions with the same semantic meaning.

The following equations and definitions may be used to express a lower bound and an upper bound.

For correct answer text passage, $a=a_{correct}$, in a semantic neighborhood called "Facet Group F," it is intended to express that an answer text passage, b, within the Facet Group F has at least one facet association and that an answer text passage, c, within another facet group, is falsely associated. Initially, it may be defined that:

$$\{a,b,c\} \in F, \text{Anchor}(F) := Q.$$

In view of {a, b, c} being a subset of representatives of answer text passages that belong to the Facet Group F, it is implicitly indicated that each of {a, b, c} have the same anchor, i.e., the anchor that establishes the neighborhood:

$$\text{score}(Q,a) \approx \text{score}(Q,b) \approx \text{score}(Q,c).$$

Step 306 may be considered to attempt to correct the model so that the scores have the following relationships:

$$\text{score}(Q,a) \approx \text{score}(Q,b)$$

$$\text{score}(Q,a) > \text{score}(Q,c)$$

$$\text{score}(Q,b) > \text{score}(Q,c).$$

Triplet loss is a known loss function for machine learning algorithms in which a reference input (called an anchor input) is compared to a matching input (called a positive input) and a non-matching input (called a negative). Using A to represent the anchor input, P to represent the positive input of the same class as A, N to represent the negative input of a different class from A, $\alpha$ to represent a margin between positive and negative pairs and $f$ to represent a function providing an embedding, triplet loss, $\mathcal{L}(A,P,N)$, may be expressed as:

$$\mathcal{L}_{(A,P,N)} = \max(\|f(A)-f(P)\|^2 - \|f(A)-f(N)\|^2 + \alpha, 0).$$

A loss function, $\mathcal{L}(Q,a,b,c)$, for the present application may be expressed, in a manner similar to the triplet loss function, as:

$$\mathcal{L}_{(Q,a,b,c)} = \max(\|E(Q,a)-E(Q,b)\|^2 - \|E(Q,a)-E(Q,c)\|^2 + \varepsilon, 0).$$

where $\varepsilon$ is used to represent a margin between b and c.

Notably, there is an important distinction between the known triplet loss function and the loss function proposed hereinbefore for the present application. Since step 306 involves sampling across a training dataset at a large scale, it may be considered to be complex to include the question text passage, Q. In other words, because the facets are extracted from datasets with groups of texts at large scale, it may be preferred to not restrict the hypothesis function, E, with the question text passage, Q, as an anchor input. Preferably, the anchor input is fluent and unknown in the training stage. Subsequently, in the deployment stage, the question text passage, Q, may be applied in runtime with an appropriate scale.

A first approach to handling a fluent and unknown anchor input involves deriving an approximate vector that is mathematically close to the question text passage, Q. A second approach to handling fluent and unknown anchor input involves ignoring the question text passage, Q, and only using the embeddings of targeted texts. A third approach to handling a fluent and unknown anchor input involves building a neighborhood based on a subspace of embeddings vectors that have been derived.

Even though the first approach may be considered to be more mathematically correct, aspects of the present application relate to use of the second approach. Points a and b may be fixed in place. A series of iterations may then be carried out. In each iteration, the hypothesis function, E, may be iteratively adjusted in a manner that attempts to minimize a loss function. Additionally, in each iteration, the soft boundaries may be iteratively readjusted (step 306).

It may be shown that the first approach would cause a problem for a robust embedding space. It may be shown that, with each iteration in the first approach, the vector Q would be caused to shift.

A projection of the question text passage, Q, onto a set of answers that form a facet group, F, may be approximated as a cluster that is centralized around a vector embedding, q, of the question text passage, Q, within the facet group.

It may be recognized that the second approach has a disadvantage in that, theoretically, upon completion of many iterative updates, the neighborhood cannot be accurately present.

Aspects of the present application relate to using minor adjustments in steps 104 and 106 to result in a lower learning rate. Aspects of the present application relate to using a small set of data to train. It has been discussed, hereinbefore, that aspects of the present application relate to using a large amount of data to stabilize the space in step 306. Accordingly, a lower learning rate in training or a small set of training data may not be considered concerning.

Aspects of the present application relate to limiting the quantity of adjustment iterations. The iterations may be defined as times of corrections of the neighborhoods. The times may be limited to, say, five. If it fails to adjust, it may be considered better to readjust the passive anchor neighborhood. Specifically, if the set of test samples are present in the last step of training, the pairing should be removed and pre-trained. Otherwise, adding a fresh set of questions related to the set of texts for better knowledge coverage.

Aspects of the present application relate to various safeguards.

In one safeguard, positive inputs may be weighted more heavily than negative inputs in the loss function.

This safeguard may be shown to be relatively easy to implement, as the neighborhood retrieved in step 306 is considered to be reliable. In a reliable neighborhood, the negative inputs, also known as "imposters" in the facet group, are expected to rarely amount to more than 30% of all of the inputs in the facet group.

In another safeguard, any facet group with an imposter ratio larger than 0.2 may be rejected as too unstable to adjust.

A further safeguard relates to only sampling one negative input from each of the facet groups (in each iteration).

With the above safeguards in place, the loss function discussed hereinbefore may be adjusted as:

$$\mathcal{L}(q, p_k, n) = \max\left(\frac{1}{k}\sum_{1}^{k}\|q - p_k\| - \|q - n\| + \varepsilon, 0\right)$$

where the vector q is representative of an embedding center of all positive inputs, $p_k$ represents an embedding of a positive input at the $k^{th}$ position and n is representative of an embedding of a negative input. The distance function, ‖ ‖, is representative of an un-normalized Euclidean distance.

In summary, the loss functions for the pre-training (step 302) include QKV softmax, MLM and NSP (transformer default). Step 302 involves pre-training the model with unsupervised language texts and medical texts on the scale of billions of tokens. The loss function for the encoding adjustment (step 304) may be implemented as a modified softmax function with a dot product. Step 304 involves adjusting the encoding of the model with semi-supervised passive anchors at the scale of a half-billion pairings. Step 304 involves adjusting the encoding of the model with supervised medical QA at the scale of 7000 pairings. The loss function for the soft boundary adjustment (step 306) may be implemented as a modified triplet loss function. Step 306 involves semi-supervised mining at the scale of millions of pairings, with around an additional 100000 pairings supervised with human corrections.

Figure 4:
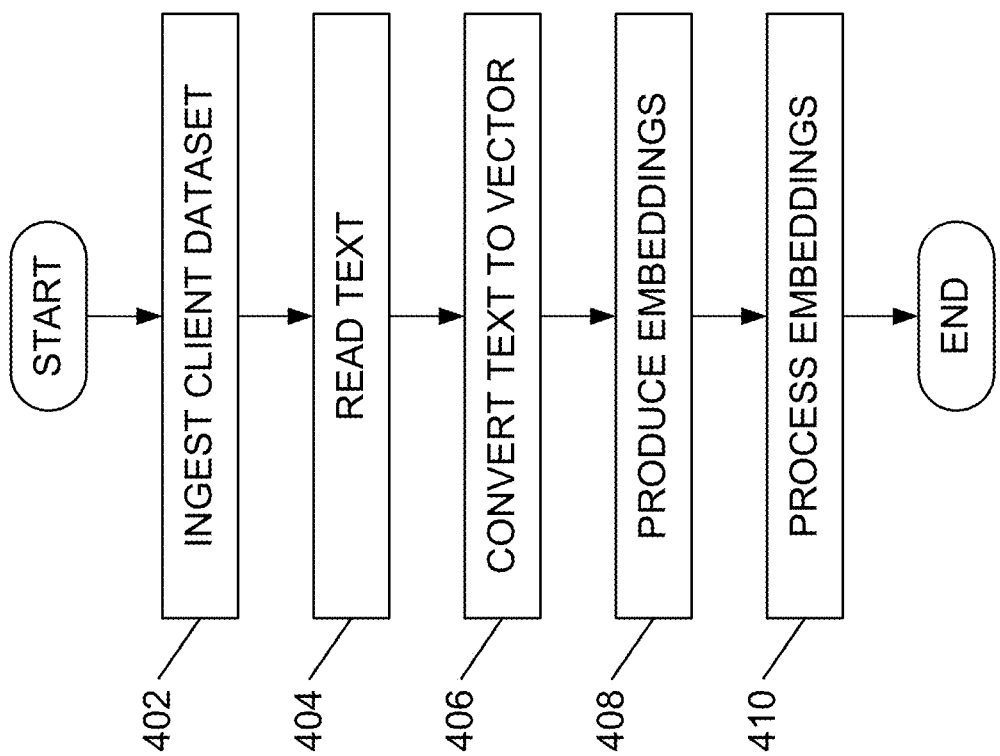
FIG. 4 illustrates example steps in the deployment (inference) stage, wherein the model of FIG. 1 is deployed, in accordance with aspects of the present application.

FIG. 4 illustrates example steps in the deployment (inference) stage, wherein the model is deployed. That is, in the deployment stage, the model is used, in runtime, to encode patient documents.

The deployment stage begins with the input unit 102 ingesting (step 402) a client dataset. The client dataset may, for example, be unstructured clinical documentation. The ingesting (step 402) may be understood to involve the input unit 102 receiving patient documents and extracting, from a client dataset, patient meta information and medical documents. The output of the ingesting (step 402) is a document.

Subsequent to the ingesting (step 402), the text converter 104 reads (step 404) text from the document. The text converter 104 then converts (step 406) the text into a vector representation.

The trained model 106 may then receive the vector representations and encode (step 408) the vector representations to produce embeddings.

The processor 108 may receive the embeddings and process (step 410) the embeddings.

The processing (step 410) of the vector representation may, for one example, involve comparing the embeddings at the output of step 408 to previously encoded embeddings of other texts.

The processing (step 410) of the vector representation may, for another example, involve clustering a first text with a second text based on the distance between the embedding representative of the first text and the embedding representative of the second text.

The processing (step 410) of the vector representation may, for another example, involve generating a journal of patient-level clinical events.

Aspects of the present application may be shown to allow for the comparison and contrasting of journals, patient to patient or groups of patients to groups of patients. Such comparison and contrasting may be shown to support use cases wherein finding similar patients is important and use cases wherein understanding similarities and differences between patient groups is useful. Such comparison and contrasting may be shown to apply well to research use cases, drug development use cases, clinical trial recruitment use cases, clinical quality improvement use cases, population health initiatives use cases and use cases associated with diversity, equity and inclusion analysis of clinical trial cohorts.

Aspects of the present application may be shown to act as a denoiser, separating what is important from what is not important, or recognizing signal vs noise. Thus, it has application in areas such as: patient identification in rare diseases; clinical trial forensics to maximize the probability of a successful trial; and clinical practice assessments to assess adherence to standards of care.

It should be appreciated that one or more steps of the embodiment methods provided herein may be performed by corresponding units or modules. For example, data may be transmitted by a transmitting unit or a transmitting module. Data may be received by a receiving unit or a receiving module. Data may be processed by a processing unit or a processing module. The respective units/modules may be hardware, software, or a combination thereof. For instance, one or more of the units/modules may be an integrated circuit, such as field programmable gate arrays (FPGAs) or application-specific integrated circuits (ASICs). It will be appreciated that where the modules are software, they may be retrieved by a processor, in whole or part as needed, individually or together for processing, in single or multiple instances as required, and that the modules themselves may include instructions for further deployment and instantiation.

Although a combination of features is shown in the illustrated embodiments, not all of them need to be combined to realize the benefits of various embodiments of this disclosure. In other words, a system or method designed according to an embodiment of this disclosure will not necessarily include all of the features shown in any one of the Figures or all of the portions schematically shown in the Figures. Moreover, selected features of one example embodiment may be combined with selected features of other example embodiments.

Although this disclosure has been described with reference to illustrative embodiments, this description is not intended to be construed in a limiting sense. Various modifications and combinations of the illustrative embodiments, as well as other embodiments of the disclosure, will be apparent to persons skilled in the art upon reference to the description. It is therefore intended that the appended claims encompass any such modifications or embodiments.

What is claimed is:

1. A method comprising:
   accessing, as text input, unstructured clinical documentation;
   converting the unstructured clinical documentation to vector representations of semantics for the text input in context of a given subdomain;
   using an artificial intelligence (AI) model to encode the vector representations to obtain embeddings representative of the text input; and
   processing the embeddings to, thereby, generate, as output, a journal specific to a patient, the journal containing a plurality of entries arranged by facet through time, wherein, for a given facet, each entry, among the plurality of entries, includes a sentence from the text input, wherein the sentence has been determined to be related to the given facet.

2. The method of claim 1, further comprising training the AI model.

3. The method of claim 2, wherein the training the AI model comprises pre-training the AI model on a language to obtain a hypothesis function and embedding boundaries.

4. The method of claim 3, wherein the pre-training the AI model comprises using a Query-Key-Value (QKV) softmax loss function.

5. The method of claim 3, wherein the pre-training the AI model comprises using a mask infill task.

6. The method of claim 3, wherein the pre-training the AI model comprises using a next sentence prediction task.

7. The method of claim 3, wherein the training the AI model further comprises adjusting the hypothesis function.

8. The method of claim 7, wherein the adjusting the hypothesis function comprises using a modified softmax function with dot product.

9. The method of claim 3, wherein the training the AI model further comprises soft adjusting the embedding boundaries.

10. The method of claim 9, wherein the soft adjusting the embedding boundaries comprises using a modified triplet loss function.

11. The method of claim 1, wherein the facet comprises an attribute of the patient.

12. The method of claim 11, wherein the attribute comprises a medication.

13. The method of claim 11, wherein the attribute comprises a comorbidity.

14. The method of claim 1, further comprising determining that the given entry is relevant to the facet.

15. The method of claim 1, wherein the given subdomain comprises an English medical subdomain.

* * * * *